United States Patent [19]

Rakhimov et al.

[11] Patent Number: 5,350,927
[45] Date of Patent: Sep. 27, 1994

[54] RADIATION EMITTING CERAMIC MATERIALS AND DEVICES CONTAINING SAME

[75] Inventors: Roustam K. Rakhimov; Elena V. Kim, both of Tashkent, Uzbekistan

[73] Assignee: Mitech Scientific Corp., Flanders, N.J.

[21] Appl. No.: 900,228

[22] Filed: Jun. 17, 1992

[51] Int. Cl.$^5$ .............................................. H05B 3/10
[52] U.S. Cl. ................................. 250/504 R; 250/503.1; 219/411; 219/553; 392/435
[58] Field of Search .............. 250/493.1, 504 R, 503.1; 219/391, 395, 406, 408, 443, 445, 458, 462, 461, 411, 553, 466, 464; 392/407, 432, 435

[56] References Cited

U.S. PATENT DOCUMENTS

| H302 | 7/1987 | Nevitt et al. ........................ 501/103 |
|---|---|---|
| Re. 32,449 | 6/1987 | Claussen et al. .................... 501/103 |
| 3,284,217 | 11/1966 | Walther ................................ 106/59 |
| 3,475,352 | 10/1966 | Barbier et al. ...................... 252/520 |
| 3,574,142 | 4/1971 | Yerouchalmi et al. ............. 252/520 |
| 3,585,390 | 6/1971 | Ishikawa . |
| 3,625,717 | 12/1971 | Grubba et al. .................... 106/39 R |
| 3,730,911 | 5/1973 | Aubin et al. ........................ 252/516 |
| 4,000,983 | 1/1977 | Alexandrov et al. .............. 29/182.5 |
| 4,045,375 | 8/1977 | Komatu ............................... 252/319 |
| 4,101,454 | 7/1978 | Kulwicki et al. ................... 252/514 |
| 4,110,260 | 8/1978 | Yamamoto et al. ................ 252/519 |
| 4,141,743 | 2/1979 | Grubba ................................ 106/66 |
| 4,330,630 | 5/1982 | Jeanovoine et al. ............... 501/105 |
| 4,551,616 | 11/1985 | Buttery . |
| 4,551,617 | 11/1985 | Crossley et al. . |
| 4,568,848 | 2/1986 | Ogawa ................................. 310/313 |
| 4,774,415 | 9/1988 | Biegel et al. ........................ 250/455.1 |
| 4,776,895 | 10/1988 | Goldstein .......................... 136/253 |
| 4,855,265 | 8/1989 | Day et al. ........................... 501/128 |
| 4,864,104 | 9/1989 | Crossley et al. . |
| 4,902,876 | 2/1990 | Mewissen . |
| 5,006,489 | 4/1991 | Nagel et al. ........................ 501/15 |
| 5,057,478 | 10/1992 | Abe et al. ........................... 502/159 |
| 5,104,830 | 4/1992 | Drouet et al. ...................... 501/9 |
| 5,130,281 | 7/1992 | Sano et al. ......................... 501/138 |
| 5,195,165 | 3/1993 | Ono et al. . |

FOREIGN PATENT DOCUMENTS

| 49-009494 | 3/1974 | Japan . |
|---|---|---|
| 49-088916 | 8/1974 | Japan . |
| 1-150527 | 6/1989 | Japan . |
| 1-227376 | 9/1989 | Japan . |
| 2-110137 | 4/1990 | Japan . |
| 4-131013 | 5/1992 | Japan . |
| 1527955 | 10/1978 | United Kingdom . |

OTHER PUBLICATIONS

Slack, G. A., "Advanced Materials for Optical Windows", GE Res. Rept. No. 79CRD071, Jun. 1979.

*Primary Examiner*—Jack I. Berman
*Assistant Examiner*—James Beyer
*Attorney, Agent, or Firm*—Pennie & Edmonds

[57] ABSTRACT

The disclosed invention is directed to novel ceramic compositions, and to stabilizer compositions for use with those ceramic compositions. The ceramic materials are formed of rare earth chromium oxides that include a novel combination of stabilizing compounds. Also, dryer or sterilizer devices which incorporate these ceramic compositions for generating infrared radiation for drying or sterilizing various articles.

23 Claims, 5 Drawing Sheets

RADIATION EMITTING CERAMIC MATERIALS AND DEVICES CONTAINING SAME

FIELD OF THE INVENTION

The invention generally relates to ceramic materials and their methods of manufacture. The invention particularly relates to refractory ceramic materials of improved thermal, chemical and physical stability and resistance to thermal cycling. The invention also relates to the use of the presently disclosed ceramic compositions in devices for drying or for fast and effective sterilization of various articles.

BACKGROUND

Ceramic materials of the formula $RCrO_3$, where R is a rare earth oxide as yttrium oxide are known in the art. See, e.g., U.S. Pat. No. 3,475,352. These materials, although useful in electroconductive applications such as electrodes, suffer from low chemical stability when exposed to high temperatures above 1600° C., low resistance to thermal cycling at temperatures above 1500° C., and the inability to be heated at high heating rates. These deficiencies have limited the use of these materials in applications where property stability is important.

A need therefore exists for rare earth oxide ceramic materials that have improved stability and which are useful in electroconductive applications as well as in high temperature environments. Such applications include the drying or sterilization of various articles.

One known method of sterilization uses infrared radiation (IR). For example, U.S. Pat. No. 4,774,415 discloses a device for sterilizing a hose coupling from a dialysis apparatus. One drawback of this device is that the source can cause insufficient sterilization of portions of the articles which do not receive the appropriate exposure of IR. If the time of sterilization is increased to compensate for the inadequate exposure, portions of the articles to be sterilized can be overheated. When articles made of metals and glass are overexposed, they can either be melted due to overheating or discolored due to oxide film formation.

Automatic regulation of the temperature by using a temperature detector and electronics for control and operation does not improve this problem because the articles often have different sizes and masses which are in conflict or incompatible with the constant and inflexible size and mass of the temperature detector. Thus, the present invention proposes to eliminate the above drawbacks and to increase the efficiency of sterilization by decreasing the sterilization time through the use of such new ceramic materials.

The drying of food products using IR produced by the use of a transforming member or screen made of mullite is known from an article by G. A. Slack entitled "Advanced Materials for Optical Windows" GE Res. Rept. No. 79CRD071, June, 1979. The primary deficiency of this method is its low drying efficiency. Thus, the present invention also proposes to increase the efficiency of IR drying methods, again through the proper selection and use of the new ceramic materials disclosed herein.

SUMMARY OF THE INVENTION

The present invention is directed to novel ceramic compositions having improved thermal, chemical and physical properties. These materials are useful in a variety of applications where rapid heating rates and property stability are important. For example, the ceramic materials of the invention may be used to generate infrared radiation of certain wavelengths.

In accordance with the invention, a ceramic composition having surprisingly stable thermal, chemical and physical properties is provided. The ceramic composition is formed of a rare earth chromium oxide and a novel composition of additives that includes alkaline earth spinels such as alkaline earth aluminate spinels, alkaline earth chromates, and, optionally, alkaline earth zirconates or alkaline earth hafniates for stabilizing the rare earth chromium oxide. The alkaline earth spinels preferably are any one of $MgAl_2O_4$, $SrO:Al_2O_3$, or $CaO:Al_2O_3$ and most preferably $MgAl_2O_4$. The alkaline earth zirconate may be $CaZrO_3$, and the alkaline earth hafniate may be $CaHfO_3$. Preferably, the stabilizing composition amounts to about 5 to 35 percent by weight, most preferably 5 to 15 percent by weight, of the ceramic composition.

The alkaline earth chromate used in the composition may be magnesium chromate, yttrium chromate, scandium chromate, terbium chromate, or ytterbium chromate, and most preferably, magnesium chromate. The rare earth chromium oxide ceramic compositions of the invention may also include at least one of an oxide of zirconium or hafnium in an amount of about 0.5 to 5 weight percent, a chromate of yttrium, scandium, ytterbium, or terbium in an amount of about 0.5 to 5 weight percent, or an oxide of cerium, dysprosium, lutetium, or europium in an amount of about 0.1 to 1 weight percent. The rare earth chromium oxide can be lanthanum chromate, neodymium chromate, samarium chromate or mixtures thereof, and most preferably is lanthanum chromate.

As mentioned, a stabilizer composition for imparting improved thermal, chemical and physical properties is included in the ceramic compositions of the invention. The stabilizer composition includes sufficient amounts of an alkaline earth spinel and an alkaline earth chromate which, in combination, stabilize the thermal, chemical and physical properties of the ceramic composition. Preferably, the alkaline earth spinel is $MgAl_2O_4$, and the alkaline earth chromate is $CaCrO_4$, $MgCrO_4$, or $SrCrO_4$. The stabilizer may further include an alkaline earth zirconate or alkaline earth hafniate such as $CaZrO_3$ or $CaHfO_3$.

The invention further is directed to silica containing compositions that also have surprisingly stable thermal, chemical and physical properties. These compositions can include $SiO_2$ in an amount of 10 to 28 weight percent and $Fe_2O_3$ in an amount of 15 to 35 weight percent, with the balance being $Cr_2O_3$. One or more of the following compounds in the following amounts may be included in these silica containing compositions: $Al_2O_3$ in an amount of about 0.5 to 3.5 weight percent, CuO in an amount of about 0.1 to 2 weight percent, CaO in an amount of about 0.5 to 15 weight percent, and MgO in an amount of about 0.1 to 3 weight percent. In these silica compositions, each of $Al_2O_3$, CuO, CaO and MgO can be present as an additive in the amount stated. Advantageously, at least two and as many as four of these additives may be present in the aforementioned amounts.

Another aspect of the present invention relates to an apparatus for drying or sterilizing articles comprising a chamber for receiving articles to be dried or sterilized; means for providing energy within the chamber; and a first ceramic material associated with the chamber for receiving and absorbing energy from the providing means and for emitting infrared radiation of one or more selective wavelengths which radiation is directed toward the articles for drying or sterilization thereof.

In this apparatus, the providing means includes an energizable element which is operatively associated with the first ceramic material such that a substantial portion of the energy generated by the element is received and absorbed by the first ceramic material. When the first ceramic material is positioned adjacent at least a portion of the energizable element, a significant portion of the energy generated by the providing means is received and absorbed by the first ceramic material. Preferably, the providing means comprises a plurality of energizable elements each having an energy emitting surface, and the first ceramic material is positioned adjacent a portion of the energy emitting surface of each element within the chamber. The first ceramic material may form a concentric tube around at least one of the elements, and, if desired, around each element, and the apparatus may include means for supporting the articles to be dried or sterilized.

For optimum operation, the apparatus further comprises a second ceramic material associated with the chamber for emitting infrared radiation of one or more wavelengths, which radiation is the same as or different from that emitted by the first ceramic material. This radiation is directed toward the articles for drying or sterilization thereof. This second ceramic material is associated with the chamber for receiving and absorbing infrared radiation from the first ceramic material, and is positioned adjacent at least a portion of the first ceramic material such that a significant portion of the infrared radiation emitted by the first ceramic material is received and absorbed by the second ceramic material. The second ceramic material should be positioned adjacent a substantial portion of the first ceramic material, such as in the form of a concentric tube around the first ceramic material. The second ceramic material may also be configured in the form of a plate which is positioned near the energizable elements to receive substantially all infrared radiation emitted from the first ceramic material.

Preferably, the energizable element comprises a halogen lamp or a high resistance wire coil within a glass tube, while first ceramic material comprises the rare earth chromium oxide ceramic composition described above, and the second ceramic material comprises the chromic oxide composition described above.

BRIEF DESCRIPTION OF THE DRAWINGS

Preferred embodiments of the dryer and sterilizer apparatus of the invention are illustrated in the attached drawing figures, wherein.

DETAILED DESCRIPTION OF THE INVENTION

Generally, the improved ceramic materials of the invention are formed from a mixture of rare earth chromium oxides and a novel combination of stabilizing compounds of an alkaline earth aluminate spinel such as $MgAl_2O_4$, an alkaline earth chromate such as $MgCrO_4$, and optional amounts of an alkaline earth zirconate such as $CaZrO_3$. This unique combination of additives enables the rare earth chromium oxide ceramic compositions of the invention to possess surprisingly increased thermal, chemical and physical properties. This unique combination of stabilizing compounds, moreover, enables the rare earth chromium oxide compounds to be heated at surprisingly high heating rates.

In accordance with the invention, electroconductive ceramic compositions formed of a mixture of rare earth chromium oxides of the formula $RCrO_3$ and a novel combination of stabilizing compounds is provided. In the formula $RCrO_3$, R is any one of lanthanum, neodymium, and samarium, preferably lanthanum or neodymium, and most preferably lanthanum.

The combination of stabilizing compounds includes alkaline earth spinels such as $MgAl_2O_4$, $SrO:Al_2O_3$, or $CaO:Al_2O_3$, most preferably $MgAl_2O_4$, an optional amount of alkaline earth zirconate or alkaline earth hafniate, preferably $CaZrO_3$ or $CaHfO_3$, and an alkaline earth chromate such as $MgCrO_4$, $SrCrO_4$, or $CaCrO_4$, and most preferably $MgCrO_4$. This combination of additives may be present in an amount of about 1–35 weight percent, and most preferably about 1.5–26 weight percent of the overall rare earth chromium oxide ceramic composition. The rare earth chromium oxide ceramic materials of the invention are illustrated by the general composition below:

| FORMULATION A | |
|---|---|
| Component | Weight Percent |
| $MgAl_2O_4$ | 0.5–10 |
| $MgCrO_4$ | 1.0–15 |
| $CaZrO_3$ | up to 10 |
| $YCrO_3$ | up to 5 |
| $ZrO_2$ | up to 5 |
| $CeO_2$ | up to 1 |
| $LaCrO_3$ | remainder |

Typically, the preparation of the chromium oxide and silica ceramic compositions of the invention is accomplished by ball milling components such as rare earth chromium oxides and stabilizer compounds in a plastic lined planet mill with Teflon balls to provide a finely ground powder. The powder is melted, ground, dried and pressed into shaped articles. The shaped articles then are sintered to provide a final product. Melting of these materials generally is accomplished under conditions which minimize the loss of oxygen from the formulated powder. Typically, the rare earth chromium oxide ceramic compositions can be melted at temperatures of about 2500° C. The silica based ceramic compositions typically can be melted at about 1900° C. Preferably, melting is accomplished in oxidizing atmospheres, most preferably air.

Sintering of the rare earth chromium oxide compositions is performed in oxidizing atmospheres at temperatures up to about 1700° C., preferably at about 1600° C. for about 12 hours. Sintering of the silica based compositions is also performed in oxidizing atmospheres at temperatures up to about 1800° C., preferably at about 1500° C. for 12 hours. Furnaces suitable for sintering at these temperatures in oxidizing atmospheres are illustrated by furnaces that employ $LaCrO_3$ heating elements. After sintering, the resultant articles are heated to high temperatures for extended time periods in oxidizing atmospheres such as at about 1500° C. to evaluate thermal, physical and mechanical properties such as compressive strength. Samples also are heated for about 20 hours at about 1600° C. to evaluate weight loss. Additional samples are metallized to evaluate specific resistance.

Samples are evaluated to measure the maximum rate which the ceramic compositions of the invention may be heated. The maximum rate of heating of the samples is based on appearance of either surface cracks or internal melting and cracking. The results of these property measurements are presented in Tables 1-11. These properties show that the ceramic materials of the invention are useful in a variety of applications where rapid heating rates and property stability are important. For example, such materials may be employed in applications directed to low temperature drying and sterilization. Additional applications include high temperature heating elements, semiconductors, thermocouples, temperature detectors and the like.

The improved properties of the ceramic compositions of the present invention are useful in devices such as dryers or sterilizers where such properties are beneficial for optimum operation. As noted above, in order to avoid overheating or oxide formation on articles to be sterilized, an appropriate quantity of IR must be generated for uniform exposure to the entire article. Since articles such as medical tools (syringes, scalpels, dental drill bits, etc), table wear (forks, knives, spoons, plates, glasses, etc), tools for food processing, instruments for the care of the human body (hair, nails, teeth, eyes, etc.), and the like have different configurations as well as different materials of construction, the IR generated for sterilization of such articles must be sufficient to sterilize the relatively larger surfaces of the articles without overheating or deteriorating the relatively smaller surfaces or those portions of the article which are made of less IR resistant materials.

As noted above, the art recognized that a ceramic screen could be used as a transforming member in an attempt to reduce the intensity of the IR to moderate its effects on the articles to be sterilized, but this often results in non-uniform sterilization. To remedy this problem, the present invention utilizes a first transforming screen made of the rare earth chromium oxide ceramic material described above as formulation A, which screen is placed in between the source of radiation and the article to be sterilized, and a second screen placed with respect to the first screen as a refractor of IR therefrom and made from a ceramic material having the following composition:

| FORMULATION B | |
|---|---|
| Component | Weight Percent |
| $SiO_2$ | 10-28 |
| $Fe_2O_3$ | 15-35 |
| CaO | up to 15 |
| $Al_2O_3$ | up to 3.5 |
| MgO | up to 3 |
| CuO | up to 2 |
| $Cr_2O_3$ | Remainder |

A sterilizer device 100 is illustrated in FIGS. 1–4. The device 100 includes an internal chamber which is accessible by a door 110 and into which is placed the articles to be sterilized. The appropriate controls 120 for the radiation sources and, if desired, the temperature of the chamber and a LED display 130, are provided in convenient locations on the front of the device.

Figure 2:
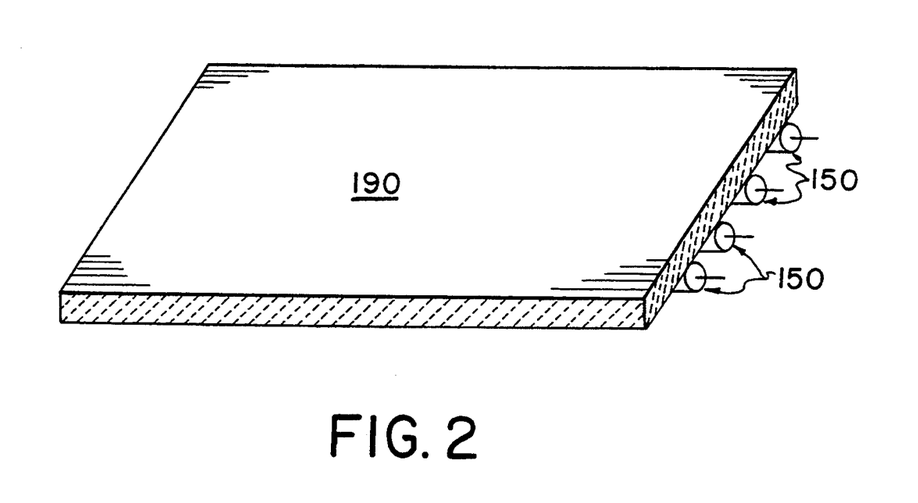
FIG. 2 is a view of an upper portion of the interior chamber of the sterilizer device of FIG. 1.
Figure 3:
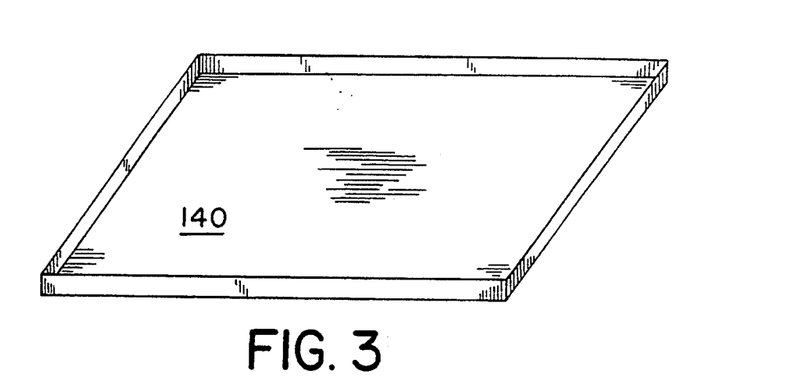
FIG. 3 is a view of a tray for holding articles to be sterilized in the device of FIG. 1.
Figure 4:
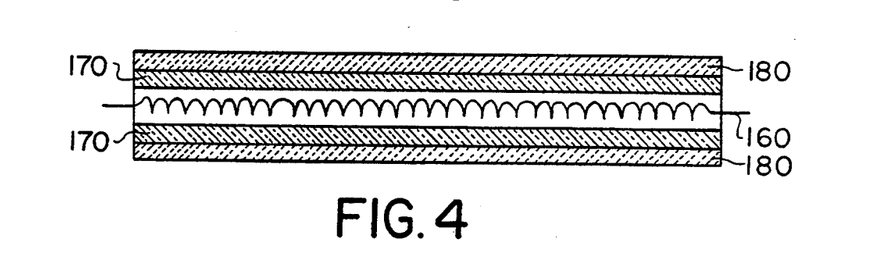
FIG. 4 is a side view, partially in cross-section of the energizing elements shown in FIG. 2.

In the chamber, as shown in FIGS. 2 and 3, a tray 140 is provided to support the articles to be sterilized. Located in an upper portion of the chamber are a number of energizable elements 150. These elements may be halogen lamps or a heating coil 160 of a high resistance material placed in a ceramic, quartz glass and/or metal tube 170.

In order to increase the sterilizing efficiency and to decrease the time of sterilization, these elements 150 are preferably provided with a concentric tube of a first ceramic material 180 for receiving and absorbing energy from the elements 150 and for emitting infrared radiation of one or more wavelengths, which radiation is subsequently directed toward the articles for sterilization thereof. This material 180 is preferably a ceramic material according to formulation A. In addition, a screen 190 of a second ceramic material, preferably a ceramic material according to formulation B, is placed above the elements for receiving and absorbing infrared radiation from the first ceramic material, and for emitting infrared radiation of one or more wavelengths which radiation is different from that emitted by the first ceramic material. This second ceramic material is positioned within the chamber so that its emitted radiation is directed toward the articles for sterilization thereof.

The ceramic compositions of the invention are also beneficial for use in drying devices. These devices have utility in a variety of applications, such as in the production of food products, plastics, ceramics, wood, bricks, leather, dishes, containers, pharmaceutical products and in other fields where it is necessary to have fast, efficient and qualitative drying with preservation of the main features of the objects that are to be dried.

Figure 1:
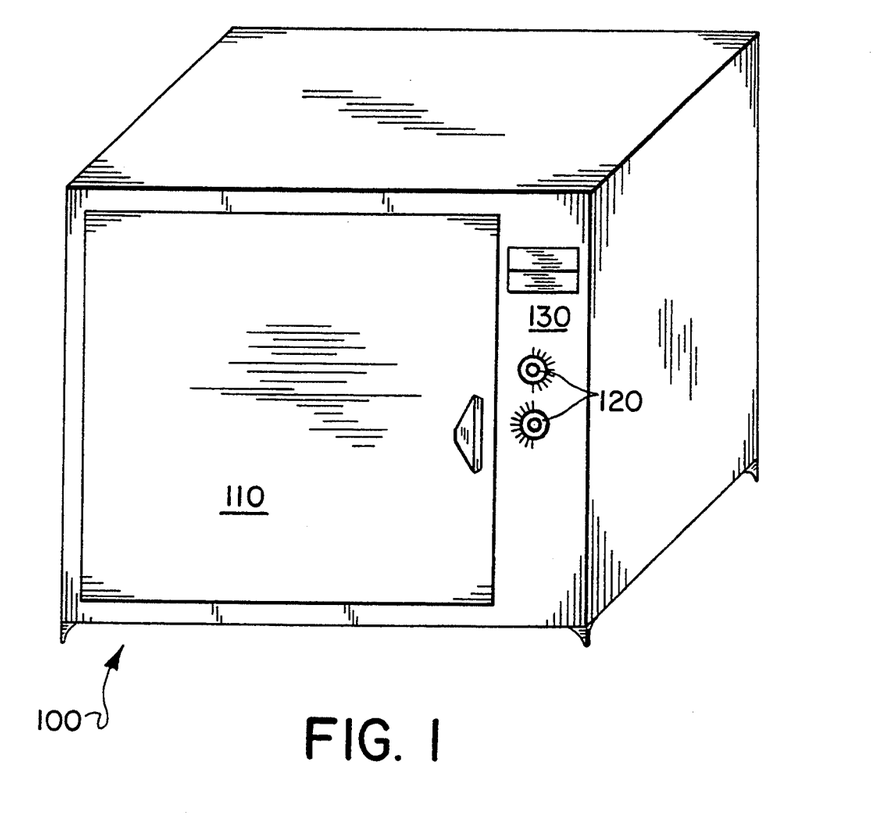
FIG. 1 is a perspective view of a sterilizer or dryer device in accordance with the invention.
Figure 5:
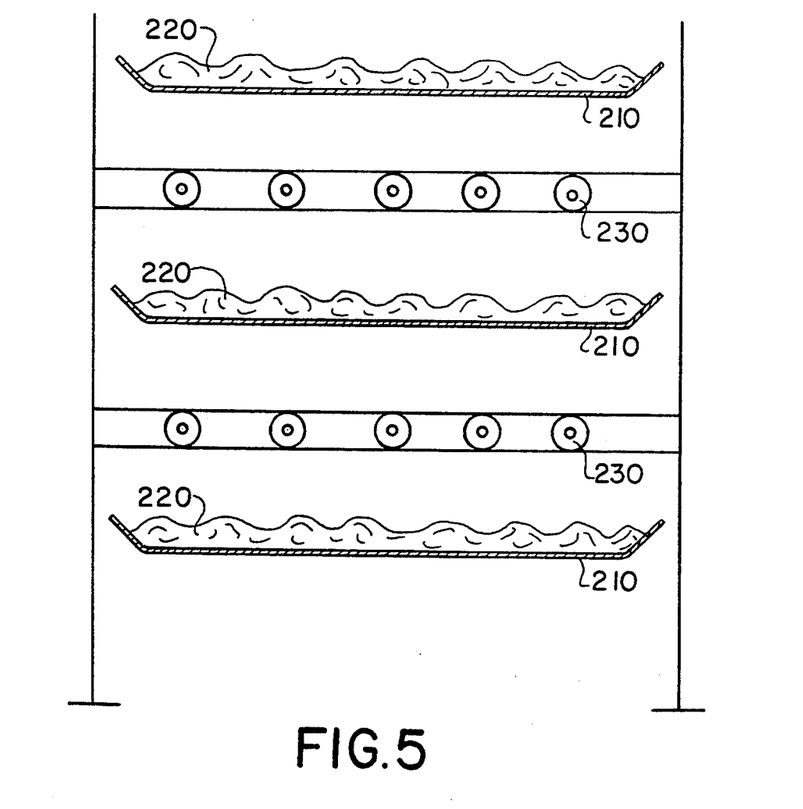
FIG. 5 is a view of the ceramic coated energizing elements and article support nets of a drying device of FIG. 1.
Figure 6:
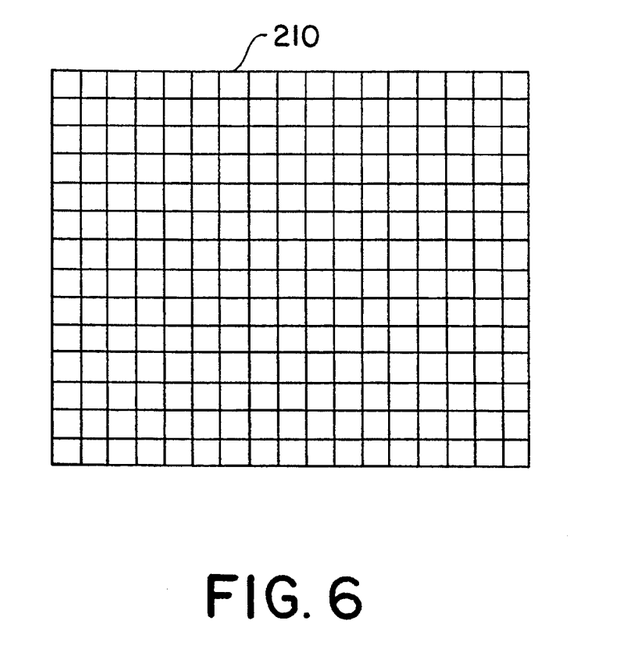
FIG. 6 is a top view of one of the support nets which hold articles to be dried in the device of FIG. 5.
Figure 7:
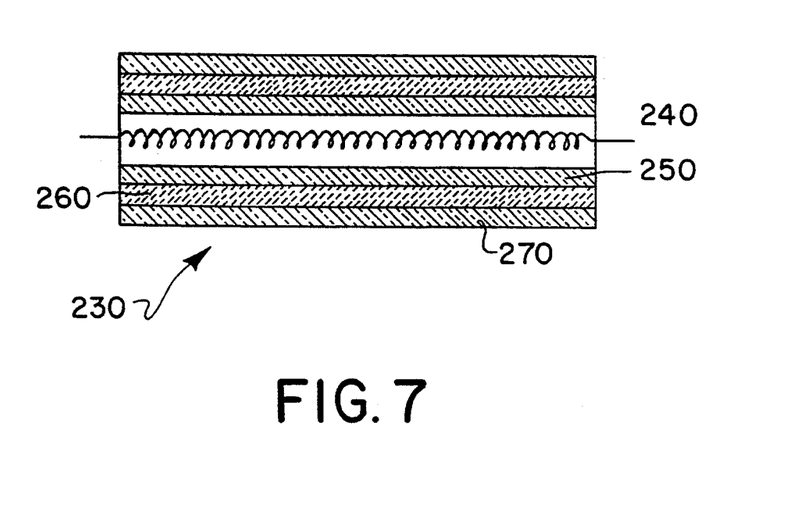
FIG. 7 is a side view, partially in cross-section of one of the energizing elements shown in FIG. 6.

One drying device is shown in FIGS. 5–7, wherein the device includes a drying chamber which is similar in external appearance to device 100 of FIG. 1. In the chamber of this device, a net or screen 210 is provided to support the objects 220 to be dried. Preferably, this net is made of a stainless steel wire mesh of suitable gauge to retain the objects to be dried thereupon. If desired, a plurality of such nets may be included within the chamber of the device. Disposed throughout the chamber are a number of energizable elements 230, as shown in FIGS. 5 and 7. These elements may be halogen lamps or a heating coil 240 of a high resistance material placed in a ceramic, quartz glass and/or metal tube 250. A transforming screen or coating of mullite or another aluminosilicate which includes a supplement of formulation A in an amount of 0.5–4.0% by weight of the composition is included within the chamber, placed adjacent the energizable elements for receiving and absorbing infrared radiation and for emitting infrared radiation of one or more wavelengths.

In another embodiment, it is possible to utilize energizable elements as disclosed above which are covered by a layer of first and second ceramic materials. In this regard, a first layer 260 of a ceramic composition, such as formulation B, is placed over the glass tube of the elements, and a second layer 270 of a ceramic composition, such as formulation A or a mixture of mullite with formulation A as defined above, is placed over the first layer 260. Preferred compositions for these ceramic layers are presented in the following examples.

Although the devices described above are specifically preferred embodiments, it should be realized that the size of the chamber, as well as the particular arrangement of the energizable elements and of the first and second ceramic materials therein, may be varied as desired by one skilled in the art, provided that a substantial portion of the infrared radiation emitted from both the first and second ceramic materials can be directed to the articles to be sterilized or dried. In addition, these devices can be used in a continuous mode, whereby the energizable elements are arranged about a conveyor belt or other movable support which carries the objects to be sterilized to, through and away from the radiation.

EXAMPLES

The invention is further described in connection with the following examples which are provided as illustrative, non-limiting embodiments thereof.

Examples 2–10 show the unexpected results obtainable with the ceramic compositions of the invention compared to a representative prior art ceramic composition (i.e., Example 1).

Example 1

(Control)

A ceramic composition with the following weight percentage components which are outside of the percent ranges of the compositions of the invention is formulated as follows:

| Component | Weight Percent |
|---|---|
| $LaCrO_3$ | 98.55 |
| $MgCrO_4$ | 0.5 |
| $MgAl_2O_4$ | 0.3 |
| $YCrO_3$ | 0.3 |
| $ZrO_2$ | 0.3 |
| $CeO_2$ | 0.05 |
| $CaZrO_3$ | 0.03 |

These components are mixed and ground in a plastic lined planet mill with Teflon balls. The resulting powder is dried, melted, re-ground and then pressed into samples having dimensions of 50×6×6 mm in the middle portion and 50×6×12 mm at the end portions for use in evaluating the maximum heating rate of the ceramic. Samples measuring 40×4×4 mm for measurement of specific resistance, and samples measuring 15 mm diameter and 15 mm high for measurement of weight loss and compressive strength were also prepared. Each of these samples is sintered in a furnace with $LaCrO_3$ heating elements at about 1600° C. for about 12 hours in air. The resulting, sintered materials then are heated for about 60 hours at about 1500° C. to evaluate compressive strength at that temperature, or for about 20 hours at about 1600° C. to evaluate weight loss.

Samples for evaluation of maximum heating rate are heated at a variety of rates. Cross-sections of these samples are inspected to identify surface cracks and internal melting. Samples heated at a rate of 5 K/min were found to be in good condition. Samples heated at a rate of 10 K/min showed cracking. As shown in Table 1, the properties of Control Example 1 given in column 1 therein are inferior to the properties of the ceramics disclosed in U.S. Pat. No. 3,475,352 given in column 6 of Table 1.

Example 2

The procedure of control Example 1 is followed with the exception that the ceramic composition employed corresponds to that of column 2 of Table 1. The resulting products have properties which surprisingly are superior to the properties of the products of U.S. Pat. No. 3,475,352 shown in column 6 of Table 1.

Example 3

The procedure of control Example 1 is followed with the exception that the ceramic composition corresponds to that of column 3 of Table 1. As shown in Table 1, the properties of the samples produced are surprisingly better than that of U.S. Pat. No. 3,475,352. Illustratively, the decrease in the compressive strength after about 60 hours of exposure at about 1500° C. is only 4.2 MPa. Further, the maximum heating rate is five times greater than that disclosed in U.S. Pat. No. 3,475,352.

Example 4

The procedure of control Example 1 is followed with the exception that the ceramic composition corresponds to Column 4 of Table 1. As shown in Table 1, the properties of the samples produced are better than those of U.S. Pat. No. 3,475,352 with the exception of specific resistance.

Example 5

The procedure of control Example 1 is followed with the exception that the ceramic composition corresponds to column 5 of Table 1. The increase in specific resistance of this example surprisingly is so great that the sample was unable to be heated to evaluate maximum heating rate.

Example 6

The procedure of control Example 1 is followed with the exception that the compositions shown in columns 1–5 of Tables 2 and 3 are employed. In the compositions of Table 2, minimal percentages of $MgAl_2O_4$ are employed whereas in Table 3, maximal amounts $MgAl_2O_4$ are employed. As can be seen from the data presented in Tables 2 and 3, the properties shown in columns 2–5 of Tables 1 and 2 exceed those of U.S. Pat. No. 3,475,352.

Example 7

The procedure of control Example 1 is followed with the exception that the compositions shown in columns 1–5 of Tables 4 and 5 are employed. In the compositions of Table 4, minimal amounts of $YCrO_3$ are employed whereas in Table 5 maximal amounts of $YCrO_3$ are employed. As shown in Tables 4 and 5, the properties of the inventive compositions shown in columns 2–5 exceed those of U.S. Pat. No. 3,475,352.

Example 8

The procedure of control Example 1 is followed with the exception that the compositions shown in columns 1–5 of Tables 6 and 7 are employed. In the compositions of Table 6, minimal amounts of $MgCr_2O_4$ are employed whereas maximal amounts of $MgCr_2O_4$ are employed in Table 7. As shown in Tables 6 and 7, the properties of the inventive compositions shown in columns 2–5 exceed those of U.S. Pat. No. 3,475,352.

Example 9

The procedure of control Example 1 is employed with the exception that the compositions shown in columns 1–5 of Tables 8 and 9 are employed. In the compositions of Table 8, minimal amounts of $CeO_2$ are employed whereas maximal amounts of $CeO_2$ are employed in Table 9. As shown in Tables 8 and 9, the properties of the inventive compositions shown in columns 2–5 exceed those of U.S. Pat. No. 3,475,352.

Example 10

The procedure of control Example 1 is employed with the exception that the compositions shown in Tables 10 and 11 are employed. In the compositions of Table 10, minimal amounts of $CaZrO_3$ are employed whereas maximal amounts of $CaZrO_3$ are employed in Table 11. As shown in columns 2–5 of Tables 10 and 11, the properties of the inventive compositions of Example 10 exceed those of U.S. Pat. No. 3,475,352.

As the foregoing examples of the invention illustrate, the invention surprisingly provides reductions in weight loss of up to three times more than that of the prior art. The invention further surprisingly provides a nine-fold decrease in the variation of compressive strength under pressure after exposure at about 1500° C. for about 60 hours. The invention moreover provides nearly an increase of 1.5 times the compressive strength and a five fold increase in the maximal rate of heating.

TABLE 1

| Components and properties | Percentage of components, weight % | | | | | |
|---|---|---|---|---|---|---|
| | 1 | 2 | 3 | 4 | 5 | 6[3] |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 292.1 | 116.0 | 7.7 | 873.4 | 2213.4 | 50–4800 |
| $\sigma Pa^1$ | 72.6 | 96.3 | 144.1 | 120.1 | 115.6 | 96–135 |
| $\sigma Pa^2$ | 18.4 | 71.4 | 140.3 | 33.2 | 26.2 | 10.2–16.1 |
| Maximal speed of heating K./min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 2

| Components and main parameters | Percentage of components, weight % | | | | | |
|---|---|---|---|---|---|---|
| | 1 | 2 | 3 | 4 | 5 | 6 |
| $MgAl_2O_4$ | 0.5 | 0.5 | 0.5 | 0.5 | 0.5 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.0 | 0.5 | 0.2 | 0.3 | 1.0 | 0.55–0.6 |
| Specific resistance, (Ohm-cm) | 304.8 | 116.0 | 7.4 | 672.3 | 1995.9 | 50–4800 |
| $\sigma Pa^1$ | 74.2 | 96.3 | 136.2 | 118.1 | 110.4 | 96–135 |
| $\sigma Pa^2$ | 18.7 | 71.4 | 130.5 | 33.1 | 25.1 | 10.2–16.1 |
| Maximal speed of heating K./min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 3

| Components and main parameters | Percentage of components, weight % | | | | | |
|---|---|---|---|---|---|---|
| | 1 | 2 | 3 | 4 | 5 | 6 |
| $MgAl_2O_4$ | 10.0 | 10.0 | 10.0 | 10.0 | 10.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 490.3 | 399.7 | 55.2 | 837.4 | 1857.8 | 50–4800 |
| $\sigma Pa^1$ | 112.6 | 98.8 | 152.8 | 120.1 | 103.2 | 96–135 |
| $\sigma Pa^2$ | 29.6 | 81.4 | 143.2 | 33.2 | 38.6 | 10.2–16.1 |
| Maximal speed of heating K./min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 4

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.5 | 0.5 | 0.5 | 0.5 | 0.5 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 270.5 | 116.0 | 35.1 | 819.5 | 2035.7 | 50–4800 |
| $\sigma Pa^1$ | 72.6 | 96.3 | 144.1 | 120.1 | 115.6 | 96–135 |
| $\sigma Pa^2$ | 18.4 | 71.4 | 140.3 | 33.2 | 26.2 | 10.2–16.1 |
| Maximal speed of | 5 | 15 | 50 | 20 | — | 10 |

TABLE 4-continued

| Components and main parameters | Percentage of components, weight % | | | | | |
|---|---|---|---|---|---|---|
| | 1 | 2 | 3 | 4 | 5 | 6 |
| heating K./min | | | | | | |

[1]Room Temperature Compressive Strength
[2]Compressive Strength after 60 hours exposure at 1500° C.
[3]Properties of U.S. Pat. No. 3,475,352

TABLE 5

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 3.0 | 3.0 | 3.0 | 3.0 | 3.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 353.8 | 220.3 | 25. | 873.4 | 2213.4 | 50–4800 |
| $\sigma Pa^1$ | 82.7 | 93.7 | 121.2 | 120.1 | 125.8 | 96–135 |
| $\sigma Pa^2$ | 19.9 | 62.8 | 87.3 | 33.2 | 28.7 | 10.2–16.1 |
| Maximal speed of heating K./min | 5 | 15 | 40 | 20 | — | 10 |

[1]Room Temperature Compressive Strength
[2]Compressive Strength after 60 hours exposure at 1500° C.
[3]Properties of U.S. Pat. No. 3,475,352

TABLE 6

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 1.0 | 1.0 | 1.0 | 1.0 | 1.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 188.5 | 116.0 | 18.0 | 867.1 | 2055.7 | 50–4800 |
| $\sigma Pa^1$ | 92.5 | 96.3 | 117.8 | 102.3 | 98.7 | 96–135 |
| $\sigma Pa^2$ | 37.4 | 51.4 | 60.3 | 21.1 | 13.1 | 10.2–16.1 |
| Maximal speed of heating K./min | 5 | 15 | 40 | 20 | — | 10 |

[1]Room Temperature Compressive Strength
[2]Compressive Strength after 60 hours exposure at 1500° C.
[3]Properties of U.S. Pat. No. 3,475,352

TABLE 7

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 15.0 | 15.0 | 15.0 | 15.0 | 15.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 282.0 | 199.0 | 22.1 | 873.4 | 2076.5 | 50–4800 |
| $\sigma Pa^1$ | 87.3 | 96.3 | 98.1 | 120.1 | 105.3 | 96–135 |
| $\sigma Pa^2$ | 81.2 | 90.6 | 90.3 | 33.2 | 25.1 | 10.2–16.1 |
| Maximal speed of heating K./min | 5 | 15 | 30 | 20 | — | 10 |

[1]Room Temperature Compressive Strength
[2]Compressive Strength after 60 hours exposure at 1500° C.
[3]Properties of U.S. Pat. No. 3,475,352

TABLE 8

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.1 | 0.1 | 0.1 | 0.1 | 0.1 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| Specific resistance, (Ohm-cm) | 297.0 | 116.0 | 8.1 | 862.1 | 2098.9 | 50–4800 |
| $\sigma Pa^1$ | 72.1 | 96.3 | 144.0 | 120.3 | 115.0 | 96–135 |
| $\sigma Pa^2$ | 18.4 | 71.4 | 140.3 | 33.2 | 26.2 | 10.2–16.1 |
| Maximal speed of heating K./min | 10 | 15 | 40 | 20 | — | 10 |

[1]Room Temperature Compressive Strength
[2]Compressive Strength after 60 hours exposure at 1500° C.
[3]Properties of U.S. Pat. No. 3,475,352

TABLE 9

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 1.0 | 1.0 | 1.0 | 1.0 | 1.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | | | BALANCE | | | |
| Weight loss, % | 1.2 | 0.5 | 0.2 | 0.3 | 1.0 | 0.55–0.6 |
| specific resistance, (Ohm-cm) | 288.0 | 110.2 | 10.6 | 873.4 | 2398.1 | 50–4800 |
| $\sigma Pa^1$ | 71.9 | 89.3 | 134.5 | 120.1 | 107.6 | 96–135 |
| $\sigma Pa^2$ | 16.7 | 67.5 | 112.4 | 33.2 | 21.5 | 10.2–16.1 |
| Maximal speed of heating | 5 | 15 | 40 | 20 | — | 10 |

TABLE 9-continued

| Components and main parameters | Percentage of components, weight % | | | | | |
|---|---|---|---|---|---|---|
| | 1 | 2 | 3 | 4 | 5 | 6 |
| K./min | | | | | | |

[1]Room Temperature Compressive Strength
[2]Compressive Strength after 60 hours exposure at 1500° C.
[3]Properties of U.S. Pat. No. 3,475,352

TABLE 10

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.05 | 0.05 | 0.05 | 0.05 | 0.05 | |
| $LaCrO_3$ | | | BALANCE | | | |
| Weight loss, % | 0.9 | 0.5 | 0.3 | 0.4 | 1.0 | 0.55-0.6 |
| Specific resistance, (Ohm-cm) | 348.0 | 116.0 | 6.6 | 717.8 | 1857.0 | 50-4800 |
| $\sigma Pa^1$ | 92.6 | 96.3 | 123.1 | 103.3 | 89.8 | 96-135 |
| $\sigma Pa^2$ | 21.3 | 71.4 | 101.6 | 36.9 | 32.2 | 10.2-16.1 |
| Maximal speed of heating K./min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 11

| Components and main parameters | Percentage of components, weight % | | | | | |
|---|---|---|---|---|---|---|
| | 1 | 2 | 3 | 4 | 5 | 6 |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.5 | 0.5 | 0.5 | 0.5 | 0.5 | |
| $LaCrO_3$ | | | BALANCE | | | |
| Weight loss, % | 0.3 | 0.3 | 0.2 | 0.3 | 1.0 | 0.55-0.6 |
| Specific resistance, (Ohm-cm) | 396.0 | 275.1 | 54.0 | 873.4 | 1985.0 | 50-4800 |
| $\sigma Pa^1$ | 96.6 | 112.3 | 152.1 | 120.1 | 109.7 | 96-135 |
| $\sigma Pa^2$ | 16.2 | 61.2 | 121.4 | 33.2 | 30.2 | 10.2-16.1 |
| Maximal speed of heating K./min | 5 | 15 | 30 | 20 | — | 10 |

[1]Room Temperature Compressive Strength
[2]Compressive Strength after 60 hours exposure at 1500° C.
[3]Properties of U.S. Pat. No. 3,475,352

The following example illustrates the use of the present ceramic compositions in a sterilization device as described above.

Example 11

Articles of medical instruments in need of sterilization were put into a chamber having the dimensions 310×175×100 mm. As a source of IR radiation, four halogen lamps were used, and these were uniformly distributed in the upper part of the chamber. The lamps are additionally covered by a layer of ceramic material of formulation A.

Above the lamps was placed a screen prepared from the ceramic material of formulation B. After turning on the power, the transforming layers begin to be heated and after a time of 1-1.5 min., the temperature of the transforming layers becomes stabilized due to thermal balance at the approximate level of 600 degrees C. In such way, the treatment of the medical instruments takes place through the IR radiation.

Results of the sterilization tests were as follows. Various medical instruments such as syringes and needles, scarificators, scalpels and pincers were then exposed to IR at 125° C. using the sterilizing device of the invention for time periods of 1, 2, 3, 5, 10 and 15 minutes, respectively. Nine separate tests were conducted for each article at each time period. It was found that each of the articles was appropriately sterilized with no indication of bacteria or viruses.

A second round of tests were conducted on the same articles for the same degree of IR and at the same time period and temperatures. Again, nine tests were made for each article at each time period. Investigations show high efficiency and reliability of the method of sterilization suggested here. It was again found that each of the articles was appropriately sterilized with no indication of antigens, HB or hepatitis B by the ROPGA method.

In comparison, the use of a prior art sterilizer device which did not include ceramic screens did not sterilize and of the 72 articles tested in the same manner as above. When the articles were properly sterilized by exposure to the IR for a period of greater than 15 minutes, many of the syringes cracked and a number of the metal articles became discolored due to local overheating of those portions of the articles.

The following example illustrates the use of the present ceramic compositions in a drying device as described above.

Example 12

An object in need of drying is prepared in accordance with its type, for example vegetables and fruits could be washed, cleaned from any rotting parts, cut if necessary and then put into the chamber of the dryer described above and then exposed to IR radiation, where the IR radiation is produced by the action of radiation of a primary source into a transforming layer or screen of the ceramic material of formulation B. As a primary source of radiation the energizable elements described above can be used.

The drying process continues until the decrease of the product mass stops. The cell mass of the product is preserved under the drying process without destruction and/or alteration. This allows the preservation of most primary property and feature of the dried product, such as its nutritious properties or features, including color, taste, smell, etc. At same time the product is dried, it is also sterilized.

When the dried product is placed into water, it takes about 15-25 minutes to re-absorb the lost water and restore its primary shape and condition, i.e. the volume, weight, taste, smell, etc.

In order to perform comparative analysis of different materials we have developed an experimental device, consisting of radiators disposed in the bottom side and a net made of stainless steel 200 mm above the radiators. The product to be dried is placed on the net.

Carrots, cut in the shape of straws with the approximate sizes of 5×5×60 mm, are exposed to a density of radiated energy (in electric power) of 3 KW/m$_2$. Drying results on these products are compared using the following elements:

(1) a conventional heat coil made of nichrome wire in a quartz glass tube, (2) a heat coil which is covered by a layer of mullite, (3) a heat coil which is covered by a single layer of a ceramic material in accordance with one embodiment of the present invention, (4) a heat coil which is covered by a single layer of a ceramic material in accordance with an another embodiment of the present invention, and (5) a heat coil which is covered by a dual layer of ceramic material in accordance with yet another embodiment of the present invention.

The ceramic layer of element (3) included the following composition:

| Formulation C | |
| --- | --- |
| Component | Weight Percent |
| $Fe_2O_3$ | 28 |
| $SiO_2$ | 17 |
| CaO | 5.5 |
| $Al_2O_3$ | 2.5 |
| MgO | 2 |
| CuO | 0.3 |
| $Cr_2O_3$ | 44.7 |

The ceramic layer of element (4) included 1% by weight of the ceramic material of formulation 2 of Table 1 with 99% by weight of mullite ("formulation D"), while the ceramic layer of element (5) included a first layer of the ceramic composition of formulation C, followed by a second layer of the ceramic material of formulation D.

Figure 8:
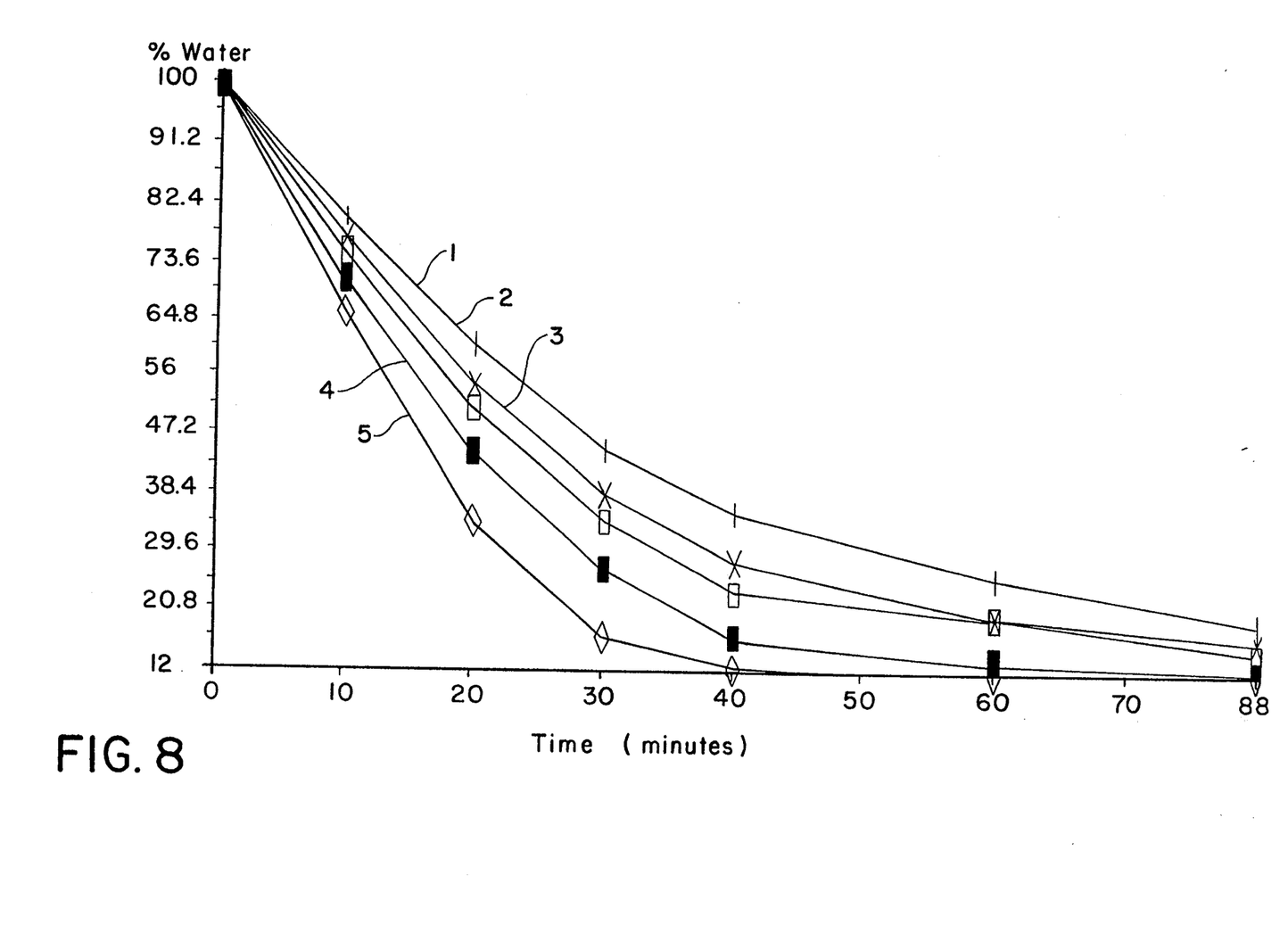
FIGS. 8-9 are graphical representations of drying results utilizing a device which incorporates dual ceramic compositions of the invention.

The various formulations having a particle size of about 1 micron were applied as a coating onto the surface of the elements using a brush together with glue made of polyvinyl spirits and/or fluid glass. Then, the elements were put into the drying device for testing. The results obtained are shown in FIG. 8.

As follows from the data presented, the maximum speed of the drying process is achieved by the consequential covering of the radiators with the two ceramic compositions (element (5)). In this case, the product being dried approaches a constant weight after about 40 minutes. Element (4) also produces a dried product after about 75 minutes. These elements have a higher drying efficiency than conventional IR drying devices.

Additional drying results on these products are compared using the following elements:

(6) a heat coil which is covered by a single layer of a ceramic material in accordance with one embodiment of the present invention, (7) a heat coil which is covered by a layer of mullite, (8) a heat coil which is covered by a single layer of a ceramic material in accordance with another embodiment of the present invention, and (9) a heat coil which is covered by a dual layer of ceramic material in accordance with yet another embodiment of the present invention.

The ceramic layer of element (6) included the following composition:

| Formulation E | |
| --- | --- |
| Component | Weight Percent |
| $Fe_2O_3$ | 35 |
| $SiO_2$ | 28 |
| CaO | 15 |
| $Al_2O_3$ | 3.5 |
| MgO | 3 |
| CuO | 2 |
| $Cr_2O_3$ | 13.5 |

The ceramic layer of element (8) included 1% by weight of the ceramic material of formulation 4 of Table 11 with 99% by weight of mullite ("formulation F"), while the ceramic layer of element (9) included a first layer of the ceramic composition of formulation E, followed by a second layer of the ceramic material of formulation F.

Figure 9:
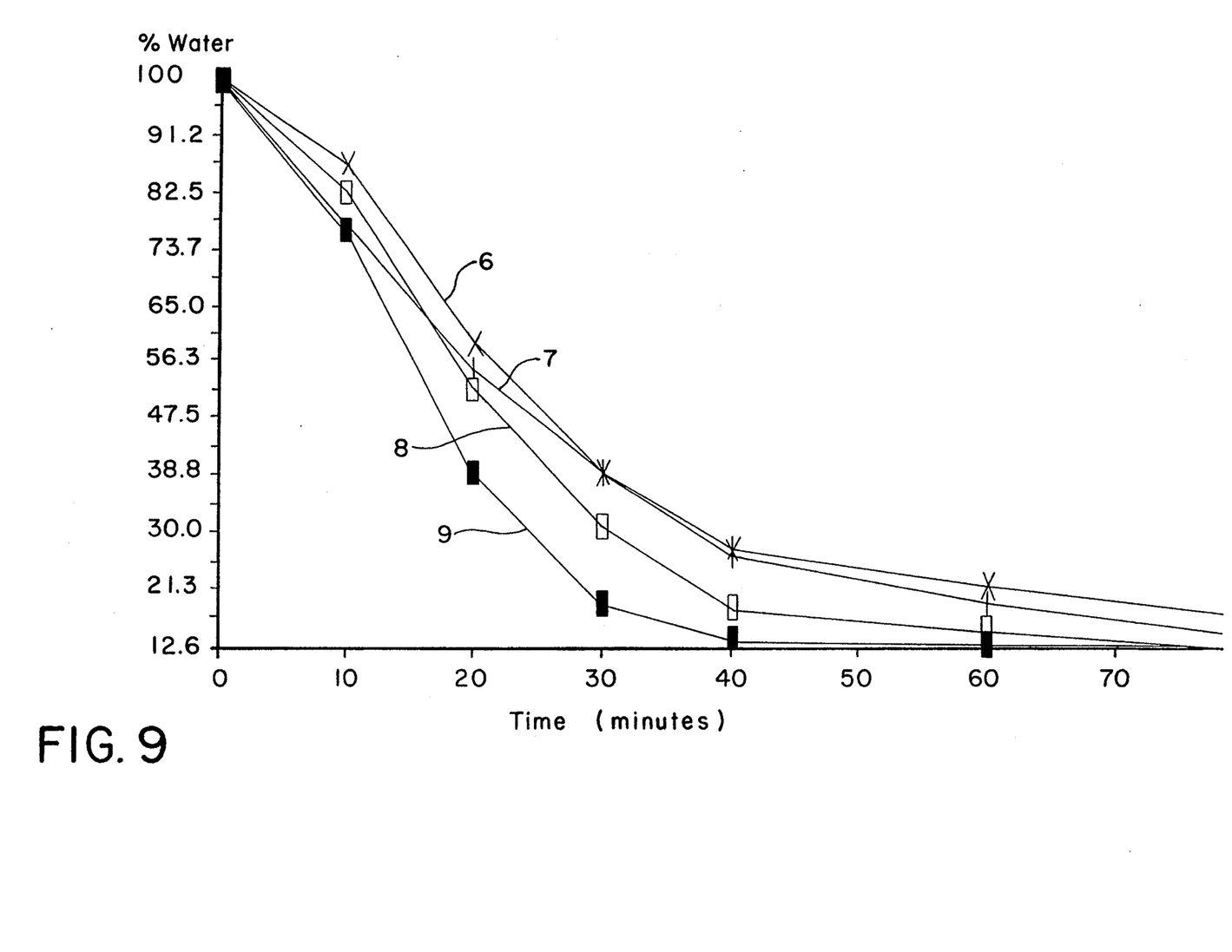

The various formulations having a particle size of about 1 micron were applied as described above, and the elements were put into the drying device for testing. The results obtained are shown in FIG. 9.

Again, the maximum speed of the drying process is achieved by the consequential covering of the radiators with the two ceramic compositions (element (9)), with the product being dried approaching a constant weight after about 40 minutes. Element (8) also produces a dried product after about 75 minutes. These elements have a higher drying efficiency than conventional drying devices.

Moreover, independent tests of dried carrots show that the present invention possess high organoleptic properties with maximum preservation of the such properties and features of the carrots, including their nutritional value and general/overall appearance in comparison with carrots dried by previously known methods.

What is claimed is:

1. An apparatus for drying or sterilizing articles comprising:
   a chamber for receiving articles to be dried or sterilized;
   means for providing energy within the chamber; and
   a first ceramic material comprising a rare earth chromium oxide composition and a stabilizing composition comprising sufficient amounts of an alkaline earth spinel and an alkaline earth chromate which, in combination, stabilize the rare earth chromium oxide composition, wherein said ceramic material is associated with the chamber for receiving and absorbing energy from the providing means and for emitting infrared radiation of one or more selective wavelengths which radiation is directed toward the articles for drying or sterilization thereof.

2. The apparatus of claim 1 wherein the providing means includes an energizable element which is operatively associated with the first material such that a substantial portion of the energy generated by the element is received and absorbed by the first ceramic material.

3. The apparatus of claim 1 wherein the first ceramic material is positioned adjacent at least a portion of the element such that a substantial portion of the energy generated by the providing means is received and absorbed by the first ceramic material.

4. The apparatus of claim 1 wherein the providing means comprises a plurality of energizable elements each having an energy emitting surface, and the first ceramic material is positioned adjacent a portion of the energy emitting surface of each of said elements within the chamber.

5. The apparatus of claim 4 wherein the first ceramic material is concentric around at least one of the elements.

6. The apparatus of claim 4 wherein the first ceramic material forms a concentric tube around each element.

7. The apparatus of claim 6 which further comprises means for supporting the articles to be dried or sterilized.

8. The apparatus of claim 1 which further comprises a second ceramic material associated with the chamber for emitting infrared radiation of one or more selective wavelengths wherein said radiation is different from radiation emitted by the first ceramic material and is directed toward the articles for drying or sterilization thereof.

9. The apparatus of claim 8 wherein the second ceramic material is associated with the chamber for receiving and absorbing infrared radiation from the first ceramic material.

10. The apparatus of claim 9 wherein the first ceramic material is positioned adjacent at least a portion of the providing means such that a substantial portion of the energy generated by the providing means is received and absorbed by the first ceramic material, and the second ceramic material is positioned adjacent at least a portion of the first ceramic material such that a portion of the infrared radiation emitted by the first ceramic material is received and absorbed by the second ceramic material.

11. The apparatus of claim 10 wherein the providing means comprises a plurality of energizable elements each having an energy emitting surface, the first ceramic material is positioned adjacent a substantial portion of the energy emitting surface of each element and the second ceramic material is positioned adjacent a substantial portion of the first ceramic material.

12. The apparatus of claim 11 wherein the first ceramic material is concentric around at least one of the elements and the second ceramic material is concentric around the first ceramic material.

13. The apparatus of claim 11 wherein the first ceramic material forms a concentric tube around each element and the second ceramic material forms a concentric tube around each tube of first ceramic material.

14. The apparatus of claim 9 which further comprises means for supporting the elements to be dried or sterilized, and wherein the providing means comprises a plurality of energizable elements each having an energy emitting surface, the first ceramic material is positioned adjacent a substantial portion of the energy emitting surface of each element within the chamber, and the second ceramic material is positioned within the chamber to receive a substantial portion of the infrared radiation emitted from the first ceramic material.

15. The apparatus of claim 14 wherein the second ceramic material is configured in the form of a plate and is positioned near the energizable elements to receive substantially all infrared radiation emitted from the first ceramic material.

16. The apparatus of claim 2 wherein the energizable element comprises at least one of either a halogen lamp or a high resistance wire coil within a glass tube.

17. The apparatus of claim 1 which further comprises a second ceramic material associated with the chamber for emitting infrared radiation of one or more selective wavelengths which radiation is different from that emitted by the first ceramic material and is directed toward the articles for drying or sterilization thereof.

18. The apparatus of claim 17 which further comprises means for supporting the articles to be dried or sterilized, and wherein the providing means comprises a plurality of energizable elements, each having an energy emitting surface, the first ceramic material is positioned adjacent a substantial portion of the energy emitting surface of each of said elements within the chamber, and the second ceramic material is positioned within the chamber to receive a substantial portion of the infrared radiation emitted from the first ceramic material.

19. An apparatus for drying or sterilizing articles comprising:
a chamber for receiving articles to be dried or sterilized;
means for providing energy within the chamber; and
a first ceramic material comprising a rare earth chromium oxide and a stabilizing composition comprising sufficient amounts of an alkaline earth spinel and an alkaline earth chromate which, in combination, stabilize the rare earth chromium oxide composition, and at least one of (a) an oxide of zirconium or hafnium in an amount of about 0.5 to 5 weight percent of the ceramic composition, (b) a chromate of yttrium, scandium, ytterbium, or terbium in an amount of about 0.5 to 5 weight percent of the ceramic composition, or (c) an oxide of cerium, dysprosium, lutetium, or europium in an amount of about 0.1 to 1 weight percent of the ceramic composition, said ceramic material associated with the chamber for receiving and absorbing energy from the providing means and for emitting infrared radiation of one or more selective wavelengths which radiation is directed toward the articles for drying or sterilization thereof.

20. An apparatus for drying or sterilizing articles comprising:
a chamber for receiving articles to be dried or sterilized;
means for providing energy within the chamber;
a first ceramic material comprising rare earth chromium oxide and a stabilizing composition comprising sufficient amounts of an alkaline earth spinel and an alkaline earth chromate which, in combination, stabilize the rare earth chromium oxide composition, the ceramic material associated with the chamber for receiving and absorbing energy from the providing means and for emitting infrared radiation of one or more selective wavelengths which radiation is directed toward the articles for drying or sterilization thereof; and
a second ceramic material comprising $Cr_2O_3$ which includes $SiO_2$, $Fe_2O_3$ and one or more of the following additives: $Al_2O_3$, $CuO$, $CaO$ or $MgO$, wherein said second ceramic material is associated with the chamber for receiving and absorbing infrared radiation from the first ceramic material and for emitting infrared radiation of one or more selective wavelengths, which radiation is different from that emitted by the first ceramic material and is directed toward the articles for drying or sterilization thereof.

21. The apparatus of claim 20 wherein the second ceramic material comprises $SiO_2$ in an amount of about 10 to 28 weight percent, $Fe_2O_3$ in an amount of about 15 to 35 weight percent, and the balance essentially $Cr_2O_3$ with one or more of the following additives: $Al_2O_3$ in an amount of about 0.5 to 3.5 weight percent, CuO in an amount of about 0.1 to 2 weight percent; CaO in an amount of about 0.5 to 15 weight percent, and MgO in an amount of about 0.1 to 3 weight percent.

22. An apparatus for drying or sterilizing articles comprising:
a chamber for receiving articles to be dried or sterilized;
means for providing energy within the chamber; and
a ceramic material comprising $Cr_2O_3$ which includes $SiO_2$, $Fe_2O_3$ and one or more of the following additives: $Al_2O_3$, CuO, CaO or MgO, wherein said ceramic material is associated with the chamber for receiving and absorbing energy from the providing means and for emitting infrared radiation of one or more selective wavelengths which radiation is directed toward the articles for drying or sterilization thereof.

23. The apparatus of claim 22 wherein the ceramic material comprises $SiO_2$ in an amount of about 10 to 28 weight percent, $Fe_2O_3$ in an amount of about 15 to 35 weight percent, and the balance essentially $Cr_2O_3$ with one or more of the following additives: $Al_2O_3$ in an amount of about 0.5 to 3.5 weight percent, CuO in an amount of about 0.1 to 2 weight percent; CaO in an amount of about 0.5 to 15 weight percent, and MgO in an amount of about 0.1 to 3 weight percent.

* * * * *